(12) United States Patent
Karlsson et al.

(10) Patent No.: US 6,392,036 B1
(45) Date of Patent: May 21, 2002

(54) DRY HEAT STERILIZATION OF A GLUCOCORTICOSTEROID

(75) Inventors: Ann-Kristin Karlsson, Staffanstorp (SE); Cheryl Larrivee-Elkins, Framingham, MA (US); Ove Molin, Huddinge (SE)

(73) Assignee: AstraZeneca AB (CH)

( * ) Notice: Subject to any disclaimer, the term of this patent is extended or adjusted under 35 U.S.C. 154(b) by 0 days.

(21) Appl. No.: 09/230,781

(22) PCT Filed: Nov. 11, 1998

(86) PCT No.: PCT/SE98/02039

§ 371 Date: Jan. 29, 1999

§ 102(e) Date: Jan. 29, 1999

(87) PCT Pub. No.: WO99/25359

PCT Pub. Date: May 27, 1999

(30) Foreign Application Priority Data

Nov. 14, 1997 (SE) ................................. 9704186

(51) Int. Cl.[7] .......................... C07J 71/00; A61K 31/58; A61K 31/56
(52) U.S. Cl. .................. 540/63; 540/84; 540/85; 514/174; 514/176; 514/177; 514/178
(58) Field of Search ................ 540/63, 84, 85; 552/581, 588, 590, 598; 514/174, 176, 177, 178

(56) References Cited

U.S. PATENT DOCUMENTS

| | | | |
|---|---|---|---|
| 3,962,430 A | | 6/1976 | O'Neill ..................... 424/185 |
| 5,192,528 A | * | 3/1993 | Radhakrishman et al. .... 424/45 |
| 5,556,964 A | * | 9/1996 | Hofstraat et al. ............. 514/63 |
| 5,837,699 A | * | 11/1998 | Sequeira et al. ............ 514/169 |
| 6,066,292 A | * | 5/2000 | Purwar .......................... 422/1 |

FOREIGN PATENT DOCUMENTS

| | | |
|---|---|---|
| WO | WO 92/11280 | 7/1992 |
| WO | WO 95/31964 | 11/1995 |
| WO | WO 96/09814 | 4/1996 |
| WO | WO 96/32095 | 10/1996 |

OTHER PUBLICATIONS

Kane, M. P. et al "Radolytic degradation of scheme for 60Co–irradiated corticosteroids" J. Pharm. Sci. vol. 72 No. 1 pp. 30–35 1983.*

Ansel, H. et al "Pharmaceutical Dosage Forms and Drug Delivery Systems" 6th edition, Williams & Wilkins, pp. 294–299 1995.*

* cited by examiner

Primary Examiner—Kathleen Kahler Fonda
Assistant Examiner—Leigh C. Maier
(74) Attorney, Agent, or Firm—Fish & Richardson PC

(57) ABSTRACT

The invention provides a process for the sterilization of a powdered form of a glucocorticosteroid, sterile glucocorticosteroids, sterile formulations containing glucocorticosteroids and use thereof in the treatment of an allergic and/or inflammatory condition of the nose or lungs.

18 Claims, No Drawings

DRY HEAT STERILIZATION OF A GLUCOCORTICOSTEROID

This application is the national stage entry under 35 USC 371 of PCT/SE98/02039 filed Nov. 11, 1998.

FIELD OF THE INVENTION

This invention relates to a process for sterilization of a powdered form of a glucocorticosteroid, sterile glucocorticosteroids, sterile formulations containing glucocorticosteroids and use thereof in the treatment of an allergic and/or inflammatory condition of the nose or lungs.

BACKGROUND OF THE INVENTION

Various methods have been proposed in the past for the sterilization of glucocorticosteroids. PT-A-69652 discloses the cold sterilization of micronized glucocorticosteroids using mixtures of ethylene oxide and carbon dioxide, since, according to PT-A-69652, steroids in powder form are not stable at temperatures above 60° C. Specific examples of glucorticosteroids are prednacindone, dexamethasone and prednisolone, and salts, esters and fluoro derivatives thereof, including dexamethasone acetate, dexamethasone phosphate, prednisolone pivalate and 9-alphafluoro prednisolone. However, ethyleneoxide is toxic and when it is used to sterilize glucocorticosteroids it has been found that the residual amounts of the ethylene oxide contravene pharmaceutical guidelines which require very low levels of residual ethylene oxide. Accordingly this method has been found to be unsuitable for producing therapeutically acceptable glucocorticosteroids and formulations thereof.

U.S. Pat No. 3,962,430 discloses a method for the production of sterile isotonic solutions of medicinal agents, which comprises adding the agent to a saturated solution of sodium chloride in water at 100° C. and then heating the mixture at 100–130° C. This method is not suitable for suspensions of fine particles of glucocorticosteroids which are intended for inhalation because the water, and the heating and cooling involved, produce unfavorable changes in the size of the particles. Indeed it can lead to the formation of bridges between the fine particles producing large, hard aggregates which will not deaggregate into the desired fine particles upon administration.

A putative alternative is dry heat sterilization. According to the European Pharmacopoeia (1996, pp. 283–4) a normal heat sterilization process runs at 180° C. for 30 min or at a minimum of 160° C. for at least 2 hours. According to Pharmacopoeia Nordica (1964, pp. 16) such a sterilization can be carried out at 140° C. for 3 hours. However at the temperatures of these processes glucocorticosteroids suffer significant degradation and are subject to changes in their surface structure.

Sterilization by β- or γ-irradiation is also known. Indeed Illum and Moeller in Arch. Pharm. Chemi. Sci., Ed. 2, 1974, pp. 167–174 recommend the use of such irradiation to sterilize glucocorticosteroids. However when such irradiation is used to sterilize certain finely divided, e.g. micronized, glucocorticosteroids, they are significantly degraded.

WO-A-96/09814 to Andaris Ltd. relates to spray-dried particles of a water-soluble material with a mass median particle size of 1 to 10 μm. The aim of the invention is to produce uniform and reproducible particles for use in dry powder inhalers. The water-soluble material is preferably a human protein or a fragment thereof, in natural or recombinant form, e.g. human serum albumin (HSA), alpha-1 antitrypsin or alcohol dehydrogenase. Also combinations of an active material with a carrier were produced e.g. budesonide and lactose. It is stated generally that the microparticles produced can be sterile without teaching how this could or would be achieved nor showing any proof thereof.

WO-A-96/32095 to Astra AB relates to a process for the preparation of respirable particles by dissolving an inhalation compound in a solvent, introducing the resulting solution containing the inhalation compound in droplet form or as a jet stream into an anti-solvent which is miscible with the solvent and which is under agitation. Budesonide with a mass median diameter (MMD) of less than 10 μm is produced with the process. There is no information in WO-A-96/32095 about sterilization or sterile particles.

WO-A-92/11280 to Instytut Farmaceutyczny relates to a method of obtaining (22R) diastereoisomer of budesonide by a condensation reaction followed by crystallizing the crude product of condensation from ethanol. The obtained 21-acetate of budesonide (22R) is hydrolyzed and the product thus obtained is crystallized from ethyl acetate. The content of (22S) diastereoisomer of budesonide is 1% or less. There is no information in WO-A-92/11280 about sterilization or sterile particles.

We have also found that attempts at terminal sterilization of the pharmaceutical formulations, especially suspensions, e.g. aqueous suspensions, of glucocorticosteroids have all proved unsatisfactory. Such suspensions can not normally be sterilized by sterile filtration as most of the particles of glucocorticosteroid will be retained on the filter. We have also shown that moist heat sterilization, e.g. steam treatment of glass vials containing the product, leads to an unacceptable change in particle size.

Various aqueous suspensions of finely divided glucocorticosteroids are known, e.g. the budesonide-containing product known as Pulmicort® nebulising suspension. (Pulmicort® is a trademark of Astra AB of Sweden). Similar formulations of fluticasone propionate are known from WO-A-95/3 1964.

Accordingly a new process for the sterilization of glucocorticosteroids (and formulations containing them) is required.

Surprisingly we have now found that effective sterilization of dry glucocorticosteroids can be carried out at a significantly lower temperature than that considered necessary for the heat sterilization of other substances. Such sterile glucocorticosteroids can be used in the preparation of sterile formulations containing them.

DESCRIPTION OF THE INVENTION

According to the invention there is provided a process for the sterilization of a glucocortisteroid, which process comprises heat treating the glucocorticosteroid in the form of a powder at a temperature of from 100 to 130° C. The process is preferably carried out at a temperature of from 110 to 120° C., more preferably at about 110° C., preferably for up to about 24 hours, more preferable up to 10 hours, e.g. from 1 to 10 hours. The process is conveniently carried out under atmospheric conditions, i.e. in air, but may also be carried out under an inert gas atmosphere, e.g. an atmosphere of argon or nitrogen.

Surprisingly we have found that this process kills many more spores when applied to the glucocorticosteroid budesonide than when applied to the comparison substance calcium stearate. Even better results were obtained with the glucocorticosteroid rofleponide.

It is believed, but we do not intend to be limited by this explanation, that the unexpectedly low temperature at which the glucocorticosteroids can be sterilized indicates that the glucocorticosteroid may provide some synergistic effect, when taken together with the heat treatment, in destroying the spores.

The glucocorticosteroid used in the invention is preferably an anti-inflammatory glucocorticosteroid, e.g. for use in nasal and oral inhalation. Examples of glucocorticosteroids which may be used in the present invention include betamethasone, fluticasone (e.g. as propionate), budesonide, tipredane, dexamethasone, beclomethasone (e.g. as dipropionate), prednisolone, fluocinolone, triamcinolone (e.g. as acetonide), mometasone (e.g. as furoate), rofleponide (e.g. as palmitate), flumethasone, flunisolide, ciclesonide, deflazacort, cortivazol,16α,17α-butylidenedioxy-6α,9α-difluoro-11β, 21-dihydroxy-pregna-1,4-diene-3 ,20-dione; 6α,9α-difluoro-11β-hydroxy-16α, 17α-butylidenedioxy-17β-methylthio-androsta-4-ene-3-one;16α,17α-butylidenedioxy-6α,9α-difluoro-11β-hydroxy-3-oxo-androsta-1,4-diene-17β-carbothioic acid S-methyl ester; methyl 9α-chloro-6α-fluoro-11β-hydroxy-16α-methyl-3-oxo-17α-propionyloxy-androsta-1,4-diene-17α-carboxylate; 6α,9α-difluoro-11β-hydroxy-16α-methyl-3-oxo-17α-propionyloxy-androsta-1,4-diene-17β-carbothioic acid S-(2-oxo-tetrahydrofuran-3-yl) ester; optionally in their pure isomeric forms (where such forms exist) and/or in the form of their esters, acetals or salts, where applicable. Suitably, use is made of mometasone furoate, beclomethasone dipropionate or fluticasone propionate or glucocorticosteroids with an asymmetric acetal structure, i.e. comprising 16α,17α-butylidenedioxy, such as budesonide, rofleponide or rofleponide palmitate. Preferably, use is made of budesonide, rofleponide or rofleponide palmitate and most preferably of budesonide.

The glucocorticosteroid is preferably used in the form of a finely divided, e.g. micronized, powder, particularly in the form of finely divided particles having a mass median diameter of less than 10 μm, more preferably less than 5 μm. The glucocorticosteroid may alternatively be in an ultra fine form, e.g. having a mass median diameter of less than 1.0 μm. The finely divided particles may be produced by conventional techniques known per se, e.g. by micronization or by direct precipitation. Information about micronization can be found e.g. in "The Theory and Practice of Industrial Pharmacy", Lachman, Liebermann and Klang, $2^{nd}$ Ed., 1976, Lea & Febiger, Philadelphia, USA.

The temperature, time, batch size and type of sterilizer used will be interdependent. Thus generally the higher the temperature used in the process according to the invention, the less time is required to sterilize the glucocorticosteroid. The process is preferably carried out for no more than 8 hours, e.g. from 1 to 8 hours, when the temperature is greater than about 110° C., more preferably no more than 4 hours. At a temperature of about 120° C. the process is preferably carried out for no more than 4 hours, e.g. from 1 to 4 hours, more preferably no more than 2 hours, e.g. from 1 to 2 hours.

At temperatures of from about 110° C. up to 130° C., a batch of 50 g of glucocorticosteroid may suitably be heat treated from 1 to 4 hours. If desired sub-batches, e.g. of 4×50 g, may be used.

The present process may be carried out such that it results in a more than log 4 reduction in the amount of heat resistant spores. The process of the present invention is suitably carried out such that it results in a log 6 reduction in the amount of heat resistant spores. The present process is preferably carried out such that it results in a more than log 6 reduction, and more preferably such that it results in a more than log 7 reduction in the amount of heat resistant spores.

A different way of characterizing the efficiency of a sterilizing process is by using the D value. The D value, also known as the $D_T$ value, is the time (in minutes) required to reduce ("kill") a standardized population of spores by 90% or 1 log cycle, i.e. to a survival fraction of $\frac{1}{10}$, at a specific temperature T (in ° C.).

The present process may be carried out such that the D value is less than about 240 min at the preselected temperature T, wherein T is in the range of from 100 to 130° C. The process of the present invention is suitably carried out such that the D value is less than 150 min at the preselected temperature T. Preferably, the process of the present invention is carried out such that the D value is less than 90 m in at the preselected temperature T, and more preferably such that the D value is less than 30 min at the preselected temperature T. T is suitably 100, 110, 120 or 130° C.

The sterilization process is desirably carried out in such a manner that all parts of the bulk of the glucocorticosteroid reaches, and is maintained within, the desired temperature for the desired time.

The present process may be carried out batch wise or continuously, preferably batch wise.

The glucocorticosteroid starting material for the process, which material may be in finely divided form, is suitably substantially dry, i.e. containing less than about 1% (w/w) of water. Preferably, the starting material for the process contains less than 0.5% (w/w) of water, and more preferably less than 0.3% (w/w) of water.

The glucocorticosteroid starting material for the process suitably has a bioburden of less than 50 CFU (colony forming units) per gram. The glucocorticosteroid starting material for the process preferably has a bioburden of less than 10 CFU per gram, more preferably of less than 1 CFU per gram.

According to the invention there is further provided a sterile glucocorticosteroid (e.g. budesonide), suitably dry and preferably in the form of finely divided particles, e.g. having a mass median diameter of less than 10 μm, and more preferably less than 5 μm.

By the term "sterile" we mean a product which meets the criteria of sterility according to the US Pharmacopoeia 23/NF18, 1995, pp. 1686–1690 and 1963–1975, and which provides a therapeutically acceptable glucocorticosteroid and formulations thereof. Further regulations for sterility of the final product include the European Pharmacopoeia (Ph. Eur. 1998, Chapters 2.6.1 and 5.1.1), the British Pharmacopoeia (BP 1993, Appendix XVI A, p. A180 and Appendix XVIII A, p. A184) and the Japanese Pharmacopoeia (JP, $13^{th}$ ed., pp. 69–71 and 181–182). Preferably, the therapeutically acceptable glucocorticosteroid and formulations thereof have been produced by a method which provides assurance of sterility according to the US Pharmacopoeia 23/NF18, 1995, pp. 1686–1690 and 1963–1975.

The glucocorticosteroid according to the invention will essentially maintain the same pharmacological activity and physico-chemical properties/its chemical purity and physical form as the starting material from which it is prepared, i.e. the degradation, and especially the chemical degradation, caused by the present sterilization process will be limited.

The glucocorticosteroid according to the invention is preferably at least 98.5% by weight pure, more preferably at least 99% by weight pure, and most preferably at least 99.2% by weight pure.

The invention further provides a sterile glucocorticosteroid, preferably an anti-inflammatory glucocorticosteroid, more preferably budesonide, rofleponide or rofleponidepalmitate, and most preferably budesonide, for use in the treatment of an allergic and/or inflammatory condition of the nose or lungs, e.g. chronic obstructive pulmonary disease (COPD), rhinitis or asthma. The invention also provides the use of such a sterile glucocorticosteroid, preferably an anti-inflammatory glucocorticosteroid, more preferably budesonide, in the manufacture of a medicament (preferably a sterile medicament) for use in the treatment of such conditions.

According to the invention there is further provided a sterile pharmaceutical formulation comprising a glucocorticosteroid in an aqueous suspension, wherein the glucocorticosteroid is preferably a sterile finely divided glucocorticosteroid, such as budesonide.

According to the invention there is also provided a sterile pharmaceutical formulation comprising a glucocorticosteroid and one or more pharmaceutically acceptable additives, diluents or carriers. Examples of such additives include surfactants, pH regulating agents, chelating agents, agents rendering the suspension isotonic and thickening agents.

To obtain an efficient dispersion of the glucocorticosteroid particles in the suspension, a surfactant may be used, optionally in combination with e.g. lecithin. The surfactants may also function as stabilizing agents in the formulations according to the present invention. Examples of suitable surfactants include non-ionic surfactants of the alkyl aryl polyether alcohol type, specifically Tyloxapol™- a polymer of 4-(1,1,3,3-tetramethylbutyl)phenol with ethylene oxide and formaldehyde. Further suitable surfactants include sorbitan derivatives, e.g. polyoxyethylene sorbitan fatty acid esters, preferably of the Polysorbate or Tween™ groups, more preferably Polysorbate 80 orpolyoxyethylene 20 sorbitan monooleate (Tween™80). Suitable surfactants also include polyoxyethylene ethers, especially polyoxyethylene alkyl ethers, preferably pentaethyleneglycol mono n-dodecylether or $C_{12}E_5$. Further suitable surfactants include poloxamers, polyoxyethylene castor oil derivatives, polyvinylalcohol and block copolymers of polyethyleneoxides, polypropyleneoxides, polybutyleneoxides and polyethyleneglycols (PEGs) or mixtures of any of these. Further suitable surfactants include polyethylene glycol derivatives, especially polyethylene glycol 660 hydroxystearate or Solutol™ HS 15, povidone, polyvinylpyrrolidone (PVP) and polyethyleneglycols (PEGs).

The surfactant may be present at about 0.002 to 2% w/w of the formulation. We prefer the polyoxyethylene sorbitan fatty acid esters to be present at about 0.005 to 0.5% w/w, poloxamers at about 0.01 to 2% w/w, and polyoxyethylene alkyl ethers or the polyoxyethylene castor oil derivatives at about 0.01 to 1.0% w/w of the formulation.

The pH of the suspension may be adjusted as required. Examples of suitable pH regulating agents are weak organic acids, e.g. citric acid, strong mineral acids, e.g. hydrochloric acid, and strong alkaline agents, e.g. NaOH. Alternatively, the pH of the system can be adjusted by balancing the acid and salt forms of buffers such as citric acid, sodium citrate, acetic acid, sodium acetate and sodium phosphate. We prefer the formulations intended for inhalation to have a pH in the range of from about 3.5 to about 6.0, more preferably from 4.0 to 5.0, and most preferably from 4.2 to 4.8.

We also prefer the formulation to contain a suitable chelating agent, e.g. disodium edetate (EDTA). The chelating agent may be present at about 0.005 to 0. 1% w/w of the formulation.

Agents which make the suspension isotonic may be added. Examples are dextrose, glycerol, mannitol, sodium chloride, potassium chloride and sodium bromide.

In order to form a stable suspension with a minimal tendency to agglomerate or form a sediment, a thickening agent may be included in the formulation. Examples of suitable thickening agents are cellulose derivatives, suitably cellulose ethers, or microcrystalline cellulose. Preferred cellulose ethers include ethylcellulose, ethylmethylcellulose, hydroxyethylcellulose, hydroxyethylmethylcellulose, hydroxyethylethylcellulose, methylcellulose, hydroxymethylcellulose, hydroxypropylcellulose, hydroxypropylmethylcellulose and carboxymethylcellulose (CMC), e.g. the sodium salt thereof. Suitable thickening agents also include cyclodextrin and dextrin. Suitable thickening agents further include xanthan gum, guar gum and carbomer. Preferred thickening agents in the formulations of the invention are povidone, polyvinylpyrrolidone (PVP) and polyethyleneglycols (PEGs).

The thickening agent may be present at about 0.1 to 3.0% w/w of the formulation. Preferably microcrystalline cellulose and sodium carboxymethyl cellulose (CMC) are present at about 0.5 to 2.5%, xanthan gum at about 0.3 to 3%, carbomer at about 0.1 to 2%, guar gum at about 0.3 to 2% and hydroxypropyl methyl cellulose at about 0.5 to 3.0%, w/w of the formulation.

In the suspension the active constituent, e.g. budesonide, is present as small particles, where at least 90% of the small particles have a mass median diameter (MMD) of less than 20 µm, suitably at least 80% less than 10 µm, preferably at least 70% less than 7 µm and most preferably at least 60% less than 4 µm.

We prefer the suspension to contain from about 0.05 to about 20 mg/ml of the glucocortiosteroid. More preferably the suspension contains from 0.08 to 10 mg/ml of the glucocorticosteroid and most preferably from 0.1 to 5 mg/ml of the glucocorticosteroid.

A sterile pharmaceutical formulation comprising a glucocorticosteroid, such as finely divided budesonide, rofleponide or rofleponide palmitate, sterilized according to the present process, can be prepared by mixing the sterilized glucocorticosteroid with any suitable additional ingredient, e.g. a surfactant, a pH regulating or chelating agent, an agent rendering the suspension isotonic or a thickening agent. All components, other than the glucocorticosteroid, can be produced by sterile filtration of their aqueous solutions. The resulting sterile suspension may be stored under an over pressure of a sterile and inert gas, e.g. nitrogen or argon, and should be filled under aseptic conditions into pre-sterilized containers to produce a sterile pharmaceutical product, e.g. using a blow/fill/seal system.

The invention further provides a method for treatment of an inflammatory condition of the nose or lungs by administering to a mammal, especially a human being, suffering from such a condition a therapeutically effective amount of a sterile glucocorticosteroid or a sterile formulation containing a glucocorticosteroid, preferably a sterile formulation containing a sterile glucocorticosteroid produced according to the present invention. More specifically, the invention provides a method for treatment of chronic obstructive pulmonary disease (COPD), rhinitis, asthma or other allergic and/or inflammatory conditions by administering to a mammal, especially a human being, suffering from such a condition a therapeutically effective amount of a sterile glucocorticosteroid or a sterile formulation containing a glucocorticosteroid, preferably a sterile formulation containing a sterile glucocorticosteroid produced according to the present invention.

EXAMPLES

The invention is illustrated by reference to the following Examples which are not intended to limit the invention.

Example 1

Experiments were carried out to determine the effect of heat treatment upon the chemical purity and physical form of samples of micronized budesonide.

Nine 50 g batches of micronized budesonide (sample nos. 2–10 in Table 1 below) were subjected to the heat treatment shown in Table 1 in a dry sterilizer, Lytzen model CB 1200. Sample 1 was not subjected to such treatment and was used as the reference sample. After the treatment the samples were analyzed for chemical and physical properties.

TABLE 1

| No. | 1 | 2 | 3 | 4 | 5 | 6 | 7 | 8 | 9 | 10 |
|---|---|---|---|---|---|---|---|---|---|---|
| Temp/° C. | — | 100 | 100 | 100 | 110 | 110 | 110 | 120 | 120 | 120 |
| Time/hours | 0 | 4 | 6 | 10 | 2 | 4 | 10 | 1 | 2 | 4 |
| Size/$\mu$m | 2.0 | 2.2 | 2.2 | 2.2 | 2.2 | 2.2 | 2.3 | 2.2 | 2.2 | 2.3 |
| Size range (10–90%)/$\mu$m | 2.6 | 2.5 | 2.5 | 2.5 | 2.5 | 2.5 | 2.5 | 2.5 | 2.5 | 2.5 |
| Epimer A/% by wt | 48.8 | 48.8 | 48.7 | 48.7 | 48.7 | 48.8 | 48.7 | 48.7 | 48.7 | 48.7 |
| Budesonide content/% by wt | 99.4 | 99.3 | 99.3 | 99.2 | 99.2 | 99.3 | 98.9 | 99.2 | 99.2 | 99.0 |
| Total of known foreign steroids | 0.13 | 0.14 | 0.16 | 0.15 | 0.16 | 0.15 | 0.18 | 0.14 | 0.15 | 0.17 |
| Total of unknown foreign steroids | 0.04 | 0.04 | 0.05 | 0.05 | 0.04 | 0.08 | 0.18 | 0.04 | 0.07 | 0.16 |

After the heat treatment there was no change in the Brunauer, Emett and Teller (BET) surface value (as measured using a Micrometrics Gemini 2375 device; see also British Standard 4359 (1969) part 1) of the budesonide or in its X-ray diffraction pattern for each sample compared to sample 1. The size for each sample was measured as the mass median diameter (MMD) using a Coulter counter.

Example 2

The sterilization of budesonide was compared with that of calcium stearate.

Samples of 0.5 g of budesonide and of 0.5 g of calcium stearate were each inoculated with 0.1 ml of a Steris *Bacillus subtilis* (*globigii*) (Lot# LG126B) spore suspension containing $1.5 \times 10^7$ spores. Each sample was subjected to a temperature of 110° C. for 3 hours and 10 min in a Baxter Constant Temperature Oven using the same technique as in Example 1. The spore population of the samples was measured and the results obtained are shown below in Table 2.

TABLE 2

| Compound | Before | After |
|---|---|---|
| Calcium stearate | $1.5 \times 10^7$ spores | $3.3 \times 10^6$ spores |
| Budesonide | $1.5 \times 10^7$ spores | <10 spores |

As a result of the heat treatment, a spore log reduction of greater than 6.2 was obtained in the inoculated sample of budesonide, whereas the log reduction was less than 0.7 in the inoculated sample of calcium stearate.

Example 3

Tests were performed to evaluate the heat resistance of various naturally occurring microorganisms.

Samples of 0.5 g of budesonide powder were each inoculated with approximately $10^2$–$10^3$ viable ATCC microorganisms in 120 ml open-ended polypropylene container. Each sample was subjected to a temperature of 110° C. for 3 hours and 10 min. The microorganism population of the samples was measured before and after heat treatment and the results obtained are shown below in Table 3.

TABLE 3

| Microorganism | Before | After |
|---|---|---|
| E. coli | 450 | 0 |
| B. subtilis ATCC 6633 | 300 | 0 |
| Salmonella typhi | 270 | 0 |
| C. albicans | 780 | 0 |
| A. niger | 260 | 0 |
| M. luteus | 300 | 0 |
| S. epidermidis | 240 | 0 |
| C. sporogenes | 160 | 0 |
| Ps. Aeruginosa | 350 | 0 |
| B. subtilis ATCC 6633 | $1.2 \times 10^5$ | $1^1$ |

[1]A singular bacillus species was found, verified by Gram stain in the $10^0$ dilution plate.

As is evident from Table 3, heat treatment of budesonide at 110° C. for 3 hours and 10 min, is an effective sterilizing method for a substantial variety of microorganisms.

Example 4

A formulation comprising finely divided budesonide sterilized by the method of Example 2, and meeting the criteria of sterility according to the US Pharmacopoeia 23/NF18, 1995, was prepared by mixing the following ingredients:

TABLE 4

| Micronized budesonide | 0.125 mg |
| Disodium edetate | 0.1 mg |
| Sodium chloride | 8.5 mg |
| Polysorbate 80 | 0.2 mg |
| Anhydrous citric acid | 0.28 mg |
| Sodium citrate | 0.5 mg |
| Purified water | to 1 ml |

All the components, other than the budesonide, were produced by sterile filtration of their aqueous solutions and an appropriate volume of the resulting suspension (about 2 ml) was filled under aseptic conditions into pre-sterilized 5 ml containers to produce a sterile product.

The resulting suspension may be stored under an overpressure of sterile nitrogen and may be filled into containers using a blow/fill/seal system.

Example 5

A sterile formulation comprising finely divided budesonide sterilized by the method of Example 2, can be prepared by mixing the following ingredients:

TABLE 5

| | |
|---|---|
| Micronized budesonide | 2–3 mg |
| Disodium edetate | 0.1 mg |
| Sodium chloride | 8.5 mg |
| Stabilizing agent | 0.02–2 mg |
| Anhydrous citric acid | 0.28 mg |
| Sodium citrate | 0.5 mg |
| Purified water | to 1 ml |

All the components, other than the budesonide, can be produced by sterile filtration of their aqueous solutions and an appropriate volume of the resulting suspension (about 2 ml) filled under aseptic conditions into pre-sterilized 5 ml containers to produce a sterile product.

The resulting suspension may be stored under an overpressure of sterile nitrogen and may be filled into containers using a blow/fill/seal system.

Example 6

5 g of micronized budesonide was inoculated with approximately 2 ml of a spore suspension of *Bacillus subtilis*.

The substance and the spore suspension were mixed and dried for approximately 3 hours at 55° C. The inoculated and dried budesonide was mixed with 20–40 g of non-inoculated micronized budesonide.

5 g portions of this sample were heat treated at 100° C., 110° C. or 120° C. in a Heraeus ST 5060 heating apparatus. A 1 g sample was withdrawn after various heating times at the respective heating temperatures. Each such 1 g sample was transferred to 10 ml of dilution medium pH 7.2. Appropriate dilutions were made in 0.1% Peptone Aqueous solution and the number of spores/g were determined by a pour plate technique according to US Pharmacopoeia 23/NF18, 1995, pp. 1681–1686, especially p. 1684.

The number of spores before heat treatment were determined in samples heated at 80° C. for 10 min in order to kill the vegetative cells.

The results are shown in Table 6, where the $D_T$ value is the amount of time in minutes required to obtain a log 1 reduction in the number of spores before and after heat treatment at the temperature T (in ° C.).

TABLE 6

| Heating at 100° C. | | | | |
|---|---|---|---|---|
| | 80° C. | Heating time at 100° C. | | |
| | 10 min | 15 min | 45 min | 75 min |
| spores/g | $6.5 \times 10^6$ | $4.8 \times 10^3$ | $7.1 \times 10^2$ | $1.7 \times 10^2$ |
| log spores/g | 6.81 | 3.68 | 2.85 | 2.23 |

$D_{100}$ = 41.5 min; correlation coefficient = −0.0996
This means that it takes 6 × 41.5 minutes to obtain a log 6 reduction in the number of spores at a temperature of 100° C.

| Heating at 110° C. | | | | |
|---|---|---|---|---|
| | 80° C. | Heating time at 110° C. | | |
| | 10 min | 5 min | 15 min | 20 min |
| spores/g | $2 \times 10^6$ | $2.08 \times 10^4$ | $9.25 \times 10^2$ | $3.55 \times 10^2$ |
| log spores/g | 6.20 | 4.32 | 2.97 | 2.55 |

$D_{110}$ = 8.3 min; correlation coefficient = −0.995
This means that it takes 6 × 8.3 minutes to obtain a log 6 reduction in the number of spores at a temperature of 110° C.

| Heating at 120° C. | | | | |
|---|---|---|---|---|
| | 80° C. | Heating time at 120° C. | | |
| | 10 min | 4 min | 6 min | 8 min |
| spores/g | $1.5 \times 10^6$ | $1.9 \times 10^2$ | $5.5 \times 10^1$ | $2 \times 10^1$ |
| log spores/g | 6.19 | 2.28 | 1.74 | 1.30 |

$D_{120}$ = 4.1 min; correlation coefficient = −0.998

This means that it takes 6×4.1 minutes to obtain a log 6 reduction in the number of spores at a temperature of 120° C.

Example 7

1 g of micronized budesonide, prednisolone and beclomethasone dipropionate and 0.5 g of rofleponide were inoculated with a different spore suspension to the one used in Example 6

The samples were heat treated at 110° C. A sample was withdrawn after various heating times. The number of sporesig were determined by a pour plate technique according to US Pharmacopoeia 23/NF18, 1995, pp. 1681–1686, especially p. 1684.

From the number of spores before and after heat treatment the log reduction of spores and decimal reduction time (time needed at a specified temperature to reduce the number of microorganisms with one log) was calculated.

The results are shown in Table 7.

TABLE 7

| Heating at 110° C. | |
|---|---|
| Glucocorticosteroid | $D_{110}$ value in min |
| Budesonide | 41 |
| Rofleponide | 9.8 |
| Beclomethasone dipropionate | 72.7 |
| Prednisolone | 73.8 |

Table 7 clearly shows that the present process is very efficient in reducing the number of spores in samples containing glucocorticosteroids. The process is especially efficient with budesonide and rofleponide. In fact analysis conducted on a full 1.0 g sample of rofleponide yielded total kill at very short cycle times(≧5 minutes at 110° C.), where a $D_{110}$ value could not be calculated.

Comparative Example 8

Irradiation

About 3 g of micronized budesonide substance stored in a plastic container, were subjected to irradiation. The substance was exposed to β-irradiation at 2.5 to 25 kGy and γ-irradiation at 8 to 32 kGy. After the exposure the budesonide content and the amount of related substances were determined by liquid chromatography. The chemical stability of budesonide was considered to be the most critical parameter to study.

TABLE 8

Stability of micronized budesonide substance during sterilization by irradiation

| Exposure Intensity (kGy) | Ref. i | β 2.5 | β 5 | β 10 | β 17 | β 25 | γ 7.8 | γ 31.9 |
|---|---|---|---|---|---|---|---|---|
| Budesonide content (%) | 99.5–99.8 | 99.1 | 98.9 | 98.9 | 98.8 | 98.8 | 97.9 | 95.0 |
| Related substances | | | | | | | | |
| Total of known foreign steroids | 0.13–0.15 | 0.19 | 0.19 | 0.18 | 0.20 | 0.21 | 0.34 | 0.51 |
| Total of unknown foreign steroids | 0.03–0.04 | 0.19 | 0.24 | 0.26 | 0.36 | 0.43 | 0.68 | 1.8 | i The analysis was done on different days and the reference was analyzed at all occasions From the results in Table 8, it can be seen that the budesonide content decreases in samples exposed to β- and γ-irradiation. Several new degradation products were observed, especially for the γ-irradiated sample. In addition the mass balance for both β- and γ-irradiated samples is poor. The budesonide content has decreased by 0.5–4.6 per cent, when exposed to β- or γ-irradiation.

It can be concluded that micronized budesonide can not be satisfactorily sterilized with β- or γ-irradiation, due to significant chemical degradation.

What is claimed is:

1. A process for the sterilization of a powder comprising a glucocorticosteroid or ester, acetal, or salt thereof, said process comprising heat treating the powder at a temperature of from 100° C. to 130° C., wherein the glucocorticosteroid or ester, acetal, or salt thereof contains an asymmetric acetal structure comprising 16α,17α-butylidenedioxy.

2. The process according to claim 1, wherein the glucocorticosteroid is an anti-inflammatory glucocorticosteroid.

3. The process according to claim 1, wherein the glucocorticosteroid or ester, acetal, or salt thereof is selected from the group consisting of budesonide, rofleponide and rofleponide palmitate.

4. The process according to claim 1, wherein the glucocorticosteroid is heat treated at a temperature of from 110 to 120° C.

5. The process according to claim 1, wherein the glucocorticosteroid is heat treated for no more than 10 hours.

6. The process according to claim 1, wherein the glucocorticosteroid is heat treated at a temperature of from about 110° C. to 130° C. for no more than 8 hours.

7. The process according to claim 6, wherein the glucocorticosteroid is heat treated at a temperature of about 120° C. for no more than 4 hours.

8. The process according to claim 6, wherein the glucocorticosteroid is heat treated at a temperature of about 120° C. for no more than 2 hours.

9. The process according to claim 1, wherein the glucocorticosteroid contains less than about 1% (w/w) of water before the heat treatment.

10. The process according to claim 1, wherein the glucocorticosteroid powder has a mass median diameter (MMD) of less than 10 μm.

11. The process according to claim 1, said process being carried out under an inert gas atmosphere.

12. The process according to claim 1, wherein the amount of heat resistant spores in the powder is reduced by more than log 6 by the heat treatment.

13. The process according to claim 1, wherein the time required to reduce by 90% a population of spores in the powder is less than about 240 minutes at a temperature of from 100° C. to 130° C.

14. The process according to claim 1, wherein the glucocorticosteroid is heat treated at a temperature of from about 110° C. to about 130° C. for no more than 4 hours.

15. The process according to claim 1, wherein the glucocorticosteroid contains less than about 0.5% (w/w) of water before the heat treatment.

16. The process according to claim 1, wherein the glucocorticosteroid powder has a mass median diameter (MMD) of less than 5 μm.

17. The process according to claim 1, wherein the amount of heat resistant spores in the powder is reduced by more than log 7 by the heat treatment.

18. The process according to claim 1, wherein the time required to reduce by 90% a population of spores in the powder is less than 90 minutes at a temperature of from 100° C. to 130° C.

* * * * *

UNITED STATES PATENT AND TRADEMARK OFFICE
CERTIFICATE OF CORRECTION

PATENT NO.    : 6,392,036 B1
DATED         : May 21, 2002
INVENTOR(S)   : Ann-Kristin Karlsson, Cheryl Larrivee-Elkins and Ove Molin It is certified that error appears in the above-identified patent and that said Letters Patent is hereby corrected as shown below:

<u>Title page,</u>
Item [73], replace "AstraZeneca AB (CH)" with -- AstraZeneca AB (SE) --.

<u>Column 1,</u>
Line 25, replace "ethyleneoxide" with -- ethylene oxide --.

<u>Column 2,</u>
Line 38, replace "WO-A-95/3 1964" with -- WO-A-95/31964 --; and
Line 51, replace "glucocortisteroid" with -- glucocorticosteroid --.

<u>Column 4,</u>
Line 13, replace "90 m in" with -- 90 min --.

<u>Column 5,</u>
Line 2, replace "rofleponidepalmitate," with -- rofleponide palmitate --;
Line 32, replace "orpolyoxyethylene" with -- or polyoxyethylene --.

<u>Column 10,</u>
Line 44, replace "sporesig" with -- spores/g --.

Signed and Sealed this

Twenty-first Day of January, 2003

JAMES E. ROGAN
*Director of the United States Patent and Trademark Office*